United States Patent
Kaner et al.

(10) Patent No.: US 6,265,615 B1
(45) Date of Patent: Jul. 24, 2001

(54) CHIRAL RECOGNITION POLYMER AND ITS USE TO SEPARATE ENANTIOMERS

(75) Inventors: Richard B. Kaner, Santa Monica; Charles M. Knobler; Hailan Guo, both of Los Angeles, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/322,327

(22) Filed: May 28, 1999

Related U.S. Application Data (63) Continuation-in-part of application No. 09/108,276, filed on Jul. 1, 1998, now abandoned.

(51) Int. Cl.$^7$ .......................... B01D 15/08; B01D 61/38; C07C 209/88
(52) U.S. Cl. .......................... 564/424; 210/649; 210/661
(58) Field of Search ................... 210/649, 661; 564/424

(56) References Cited

U.S. PATENT DOCUMENTS 5,077,217 * 12/1991 Matson et al. ................... 435/280
5,096,586 * 3/1992 Kaner et al. ...................... 210/500.37

FOREIGN PATENT DOCUMENTS 9804514 2/1998 (WO) .

OTHER PUBLICATIONS

Database WPI, Section Ch, Week 8628, Derwent Publications Ltd., London, GB, Class A35, AN 86–181322, XP002116880, & SE 8 404 967 A (Mosbach), Apr. 5, 1986 (Apr. 4, 1986), Abstract.

H. Guo et al., "Chiral separation of amino acids based on a new chiral recognition polymer", Polymer Preprints, vol. 40, No. 1, Mar. 1999, pp. 506–507, XP002116879, whole document.

M.R. Majidi et al., "Chemical generation of optically active polyaniline via the doping of emeraldine base with (+) – or (–)–camphorsulfonic acid", Polymer., vol. 36, No. 18. 1995, pp. 3597–3599.

E.E. Havinga et al., "Large induced optical activity in the conduction band of polyaniline doped with (1S)–(+)–10–camphorsulfonic acid", Elsevier Science S.A., vol. 66, 1994, pp. 93–97.

Mir Reza Majidi et al., "Enantioselective electropolymerization of aniline in the presence of (+)– or (–)–camphorsulfonate ion: a facile route to conducting polymers with preferred one–screw–sense helicity", Polymer, vol. 35, No. 14, 1994, pp. 3113–3115.

Mir Reza Majidi et al., "Facile synthesis of optically active polyaniline and polytoluidine", Polymer, vol. 37, No. 2, 1996, pp. 359–362.

Wu–Song Huang et al., Polyaniline, a Novel Conducting Polymer: Morphology and Chemistry of its Oxidation and Reduction in Aqueous Electrolytes, J. Chem. Soc., Faraday Trans. 1, 1986, 82, pp. 2385–2400.

Mark R. Anderson et al., "Conjugated Polymer Films for Gas Separations", American Associate for the Advancement of Science, vol. 252, Jun. 7, 1991, pp. 1412–14515.

* cited by examiner

*Primary Examiner*—Taofiq A. Solola
(74) *Attorney, Agent, or Firm*—Koppel & Jacobs; Michael J. Ram (57) ABSTRACT

A new polymeric material, a process for forming the material and method of using the material to separate enantiomers of chiral compounds, particularly amino acids and pharmaceuticals are disclosed.

A polymeric material can be formed from polyaniline doped with a chiral acid and then extracted with a suitable base. This leaves behind a polymeric material which preferentially traps, and then selectively releases, one enantiomer of a chiral mixture brought in contact with the surface of the polymeric material. In particular, when polyaniline is doped with either R- or S-camphorsulfonic acid (CSA) it takes on a chiral structure. Removing the chiral acid dopant leads to a new chiral polyaniline. The dedoped chiral polyanilines have the ability to discriminate among enantiomers of many compounds which exist in chiral mixtures.

17 Claims, 9 Drawing Sheets

------ R-CSA DEDOPED + L-PHENYLALANINE + ISOPROPANOL
---- R-CSA DEDOPED + L-PHENYLALANINE
——— R-CSA DEDOPED FILM

——— BEFORE REACTION
--------- AFTER REACTION

——— BEFORE REACTION
----- AFTER REACTION

CHIRAL RECOGNITION POLYMER AND ITS USE TO SEPARATE ENANTIOMERS

This application is a continuation-in-part application of application Ser. No. 09/108,276, filed Jul. 1, 1998, now abandoned which application is hereby incorporated by reference in its entirety.

This invention was made in part with government support from the following: Office of Naval Research, Grant Nos. N00014-93-1-1307 and N00014-97-1-0888 and U.S. Los Alamos National Laboratory, Grant No. STB-UC: 97-192.

BACKGROUND OF THE INVENTION

The present invention relates to the separation of chiral compounds and a unique polymer film or powder and process using these materials to perform this separation. In particular, the invention relates to separation of enantiomers of pharmaceutical compounds or amino acids.

Enantioseparations are becoming increasingly important because the U.S. Food and Drug Administration has declared that if a drug is chiral, the biological effects of both enantiomers must be determined; Stinson, S. C. "Chiral Drugs", Chem. Eng News 1995, 73, 41; Collins, A. N., Sheldrake, G. N. & Crosby, J. "Chirality in Industry" (Wiley & Sons, Chichester), 1992.) Many procedures for resolution of D, L-amino acids have been documented (Turk, J., Panse, G. T. Marshall, G. R." Studies with a-methyl amino acid resolution and amino protection", J. Org. Chem. 1975, 40, 953; Meijer, E. M., Boesten, W. H. J., Schomaker, H. E., Van Balken, J. A. M. "Use of biocatalyst in the industrial production of specialty chemicals" Biocatalysis in organic synthesis. (Tramper, J., Van Der Plas, H. C., Linko, P., Eds). Amsterdam: Elsevier, 1985,135; Schutt, H., Schmidt-Kastner, G., Arens, A., Preiss, M. "Preparation of optically active D-arylglycines for use as side chains for semisynthetic penicillins and cephalsoporins using immobilized subtilisins in two-phase systems" Biotech. Bioeng. 1985,27, 420; Moller, A., Syldatk, C., Schulze, M., Wagner, F. "Stereo- and substrate-specificity of a D-hydantoinase and a D-N-carbamyl-amino acid amidohydrolase of Arthrobacter crystallopoietes AM2," Enzyme Microb. Technol. 10:618–625; Wong, C. H., Chen, S. T., Hennen, W. J., Wang, Y. F., Liu, J. L. -C., Pantoliano, M. W., Whitlow, M., Bryan, P. N. "Enzymes in organic synthesis: Use of subtilisin and a highly stable mutant derived form multiple site specific mutations", J. Am. Chem. Soc. 1990, 112, 945; Sato, T. Tosa, T. "Optical resolution of racemic amino acids by aminoacylase", Industrial Application of Immobilized Biocatalysts.(Tanaka, A., Tosa, T., Kobayashi, T., Eds.) Marcel Dekker, New York: 1993,3).

D-amino acids along with unnatural amino acids have found extensive application as antibiotic peptides, and as synthetic peptides with enhanced hormonal or neural activity. (Folkers, K., Hoerig, J., Rosell, S., Bjoerkroth, U. "Chemical design of antagonists of substance P: Acta Physiol. Scand. 1981, 111, 505; Manavalan, P., Momany, F. A. "Conformational studies on the enkephalin releasing peptides, tyr-arg and tyr-d-arg", Biochem. Biophys. Res. Commun. 1982, 105(3), 847: Blanc, J. P., Kaiser, E. T. "Biological and physical properties of a b-endorphin analog containing only D-amino acids in the amphophilic helical segment 13–31", J. Biol. Chem. 259(15): 9549–9556. Most of these unnatural amino acids are unavailable through fermentation. Resolution is an effective means of producing optically pure unnatural amino acids. Traditionally, racemate amino acids can be resolved by entrainment with enzymes or bacteria, or by using chiral stationary phase liquid chromatography (LC) or high performance liquid chromatography (HPLC). These methods are limited by the economic costs as well as the difficulty of scale up to commercially viable processes. Liquid membranes have also been reported in the literature to be used for enantioseparations of racemate amino acids but so far have shown poor separating abilities.

Additionally, certain pharmaceutical compounds are known to provide effective treatment against disease states or to ameliorate medical conditions. These compounds often occur as a chiral mixture where one enantiomeric form is more effective for its intended purpose than other enantiomeric forms of the same compounds. In fact, certain enantiomeric forms may act to counteract the beneficial effects of other enantiomeric forms. Therefore, it is highly beneficial to be able to separate out and collect the most effective forms of enantiomeric compounds.

There presently are no readily universal techniques or materials which are available for the general separation of chiral compounds. As indicated above, there is a need for a process and materials which will allow a broad range of different chiral materials to be consistently separated in an economical, quantitative and high purity manner.

SUMMARY

It has been found that a membrane can be formed from polyaniline doped with a chiral acid and then extracted with a suitable base. This leaves behind a polymeric film which preferentially traps, and then selectively releases, one enantiomer of a chiral mixture brought in contact with the film surface. In particular, when polyaniline is doped with either R- or S-camphorsulfonic acid (CSA) it takes on a chiral structure. Removing the chiral acid dopant leads to a new form of chiral polyaniline. These chiral dedoped polyanilines have the ability to discriminate among enantiomers of various compounds such as DL-dopa, DL-amphetamine sulfate, or amino acids, for example, DL-phenylalanine.

A BRIEF DESCRIPTION OF THE DRAWINGS

These and other features, aspects and advantages of the present invention will become better understood with reference to the following description, appended claims, and accompanying drawings, where:

DESCRIPTION

A new chiral recognition polymer and a method for its use have been developed which can enantioseparate solutions of racemic mixtures. The chiral recognition polymer comprises a polymer which can be doped with a chiral acid and then treated to remove the dopant such that the recognition polymer retains its molecular orientation, which includes holes or sites where the dopant had been situated. As a result of the extraction procedure, the dedoped polymer preferentially traps one chiral orientation from a racemic mixture of a compound. For the purposes of this description and to distinguish the starting polymer from a material of the same chemical formulation but different structure on a molecular or microscopic level, the starting polymer will be referred to as "achiral", following addition of the dopant it will be referred to as the "doped" polymer, the polymer following removal of the dopant will be referred to as the "dedoped" polymer and the reactived polymer following acid treatment will be referred to as the "redoped" polymer.

To prepare the chiral recognition polymer, an achiral conjugated polymer that can be readily doped by an acid is used. A particularly suitable material is polyaniline. Polyaniline is both air and thermally stable in both its doped and dedoped forms. Applicants have developed this polymer over the past ten years for use in gas and liquid separation techniques (U.S. Pat. No. 5,096,586 issued Mar. 17, 1992; U.S. Pat. No. 5,358,556 issued Oct. 25, 1994; Mark R. Anderson, Benjamin R. Mattes, Howard Reiss, Richard B. Kaner, "Conjugated polymer films for gas separation", Science, 1991, 252, 1412; J. A. Conklin, T. M. Su, S. C. Huang, R. B. Kaner, "Gas and Liquid Separation Applications of Polyaniline Membranes", Handbook of Conducting Polymers (T. A. Skotheim, R. L. Elsenbaumer, J. R. Reynolds Eds). Marcel Dekker, Inc. New York, 1998, 945). Controlling the doping level in polyaniline has led to highly selective membranes for discriminating among important gases (Anderson M. R.; Mattes, B. R.; Reiss, H.; Kaner, R. B. Science 1992, 252,1412; Kuwabata, S.; Martin, C. R. J. Membr. Sci. 1994, 91, 1; Rebattet, L.; Escoubes, M.; Pineri, M.; J. Appl. Polym. Sci. 1995, 57 1595; Mattes, B. R.; Anderson, M. R.; Conklin, J. A.; Reiss, H.; Kaner, R. B. Synth. Met. 1993, 55–57, 3655. and separating liquids by pervaporation. (Conklin, J. A.; Su, T. M.; Huang, S. C.; Kaner, R. B., Handbook of Conducting Polymers; Ed. Skotheim, T. A.; Elsenbaumer and Reynolds, J. R. Marcel Dekker, Inc., New York, 1998). In gas permeability experiments it has been demonstrated that removing dopants increases the free-volume in polyaniline membranes leading to higher gas throughput. The synthesis of chiral polyaniline (Majidi, M. R.; Kane-Maquye, L. A. P; Wallace, G. G. Polymer, 1994, 35, 3113; Havinga, E. E.; Bouman, M. M.; Meijer, E.W.; Pomp, A.; Simenon, M. M., J. Synth. Met. 1994, 66, 93; Majidi, M. R.; Kane-Maquire, L. A. P; Wallace, G. G. Polymer, 1995, 36, 3597; Majidi, M. R.; Kane-Maquire, L. A. P; Wallace, G.G. Polymer, 1996,37, 359; MacDiarmid, A. G. Synth. Met. 1997, 84, 27) opens up the possibility of separating left- and right-handed enantiomers from a racemic mixture. Chirality in conjugated polymers was first demonstrated with polyacetylene (F. Ciardelli, E. Benedetti, O. Pieroni, Makromol. Chem. 1967, 103, 1; F. Ciardelli, S. Lanzillo, O. Pieroni, Macromolecules 1974, 7, 2; T. Aoki, K. -I. Shinohara, T. Kaneko, E. Oikawa, Molecules 1996, 29, 4192; E. Yashima, S. Huang, Y. Okamoto, J. Chem. Soc. Chem. Commun. 1994, 1811) and polypyrrole (Salmon, M. Brian, G. J. Electrochem. Soc. 1985, 132, 1897; Elsenbaumer, R. L.; Eckhardt, H.; Eqbal, Z.; Toth, J.; Baughman, R. H. Mol. Cryst. Liq. Cryst. 1988, 118, 111) and then polythiophene (Lemaire M.; Delabouglise, D.; Farreau, R.; Guy, A.; Roncali, J., J. Chem. Soc., Chem. Commun., 1988, 658; Kotkar, D.; Joshi, V. Ghosh, P. K. J. Chem. Soc. Chem. Commun. 1988, 917.

Polyaniline has the advantage of a simple acid/base doping/dedoping chemistry which enables dopants to be readily removed. When the chiral dopants are removed from polyaniline films, the polyaniline is still chiral since there is little driving force for the chain conformations to relax.

This dedoped polyaniline possesses chirality which is markedly different from that of the doped form of polyaniline. This new dedoped optically active form of polyaniline possesses a unique chiral recognition ability when exposed to a racemic mixture of selected compounds such as amino acids. Further, the amino acid enantiomer which becomes bound by the chiral polyaniline can be released using an organic solvent. This enables a treated enantiomeric mixture of amino acids, such as DL-phenylalanine, to be separated into its D- and L-constituents.

It has now been found that polyaniline can be doped using a strong acid that is chiral, such as R- or S-camphorsulfonic acid. The chiral acid attaches to the basic sites on the polyaniline with up to one acid unit for every two monomer units. Once the polymer is doped with a chiral acid the polymer becomes chiral (M. R. Majidi, L. A. P. Kane-Naguire and G. G. Wallace, "Facile Synthesis of Optically Active Polyaniline and Polytoluidine," *Polymer,* 1995 36 3597. ). However, Majidi et al. did not suggest dedoping the chiral polymer or the unique properties of that polymer once dedoped. Treating the chiral-acid-doped polymer with a base readily removes the acid dopant and leaves behind polyaniline that is still chiral (dedoped polyaniline). It is believed that the new, dedoped form of polyaniline has a chiral pocket that can strongly interact with or capture one enantiomeric form of an amino acid or other enantiomeric compounds in a racemic mixture. As a result, the dedoped chiral form of polyaniline can be used as a chiral recognition polymer and allows the quantitative and selective separation of an appropriate enantiomeric form from a racemic mixture of organic compounds. In particular, the dedoped polymer can be used for both analytical and preparative purposes in aqueous and alcohol solutions of racemic mixtures without the need for the addition of buffer solutions.

The preparation of the dedoped polymer is easy to scale-up to commercial scale operations and has a capacity to recognize and separate chiral materials significantly superior to natural biopolymers, such as Human Serum Albumin (HSA) and Bovine Serum Albumin (BSA), used for chiral separations in the past. Additionally, the chiral recognition polymer can be reusable for the separation of the same or other chiral materials and can be used to sense the existence of chiral materials.

One method of employing dedoped chiral polyaniline is the separation of enantiomers using a flow-through column, similar to a liquid chromatography column, enclosing the dedoped polymer in a manner so that it presents a high surface area of the polymer to solutions containing the chiral mixture which are flowed therethrough. This has been achieved by forming thin polymer coatings on silica beads designed for use in column chromatography. To ensure that the polyaniline adheres strongly to the silica beads, the surface of the beads is first silanized using dichlorodiphenyl silane or related compounds such as dichlorodibenzyl silane. This is accomplished by soaking the beads in toluene solution of the silane for 40 mins. followed by washing with toluene three times to remove any nonconvalently bonded silane. The silanized silica beads are then dried at 60° C. under vacuum for 12 hours and a thin chiral doped polyaniline film is deposited on the beads. To do so, polyaniline powder previously synthesized through an acid-catalyzed oxidation (W. S. Huang, B. D. Humphrey, A. G. MacDiarmid, *J. Chem. Soc. Faraday Trans.* 1986, 82, 2385.) is dispersed in a camphorsulfonic acid/N-methylpyrrolidinone (NMP) solution and the silica beads are coated with this solution. This procedure leaves a doped polymer film approximately 1–2 μm thick deposited on the surface of the beads. The coated beads are then washed 4 times with 0.1 M ammonium hydroxide to remove the chiral dopant and the beads are packed into a column (100×4.6 mm or 250×4.6 mm) for use in chiral separations. An alternative process is to grind the doped or dedoped polymer into a powder and contact the chiral mixture with the dedoped powdered polymer. However, it is preferred to grind the doped film as extraction of the acid proceeds most rapidly with the powdered form. As a further alternative, the powdered product can be produced by spray drying or vacuum flash drying the doped solution to produce a powdered, doped polyaniline material. Other techniques for forming dry powdered product from liquid or solvent mixtures are also applicable.

If use of the dedoped film results in lessening of the separation capability over a period of time, the doping process as set forth above can be repeated on the polymer coating to form a redoped film. Alternatively, exposure of the dedoped film, as described below, to any strong acid will reactivate the polymer to its doped form. Then the redoped film can be extracted, in the same manner with a base to reactivate.

Figure 1:
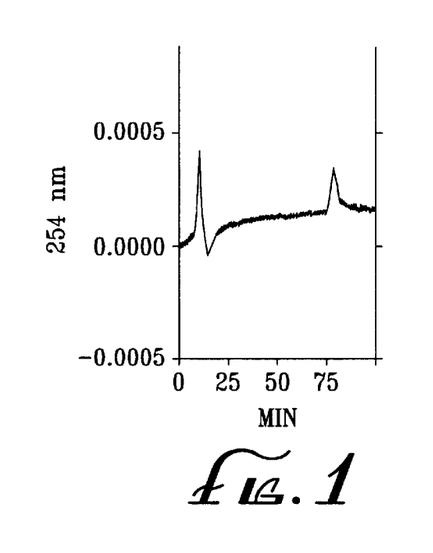
FIG. 1 is a graph of the HPLC separation of DL-phenylalanine using a 250 mm×4.6 mm column with R-CSA doped/dedoped polyaniline as the chiral stationary phase and with isopropanol as the eluent.
Figure 2:
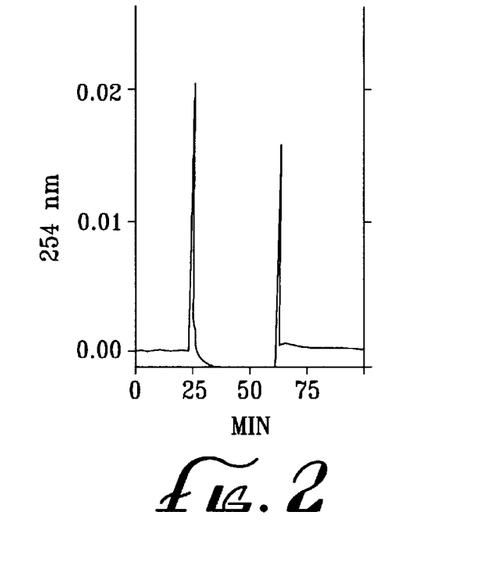
FIG. 2 is a graph of the HPLC separation of an aminoalcohol derived from DL-tyrosine using a 100 mm×4.6 mm column with R-CSA doped/dedoped polyaniline as the chiral statinary phase with water and then isopropanol as the eluents.

For example, the dedoped form of R-CSA polyaniline preferentially interacts with L-phenylalanine as indicated by a "doping" type absorption observed at 450 nm in circular dichroism spectra. Since the dedoped form of R-CSA polyaniline does not complex with D-phenylaniline, this chiral polymer can be used to separate a racemic mixture of DL-phenylalanine and related compounds. Moreover, the amino acid enantiomer bound by the chiral polyaniline can be released by an organic solvent. Using a 250 mm column (FIG. 1) packed with beads prepared as indicated above, the separation factor (α) for DL-phenylalanine from an aqueous solution is 8.4 and for DL-$PhCH_2CH(NH_2)CH_2OH$ using the 100 mm column is α=2.6 (FIG. 2). An α>2 is considered to be useful industrially; an α of 8.4 far exceeds the minimum necessary to cause a successful separation and the α of 2.6 is acceptable for commercial uses.

Figure 3:
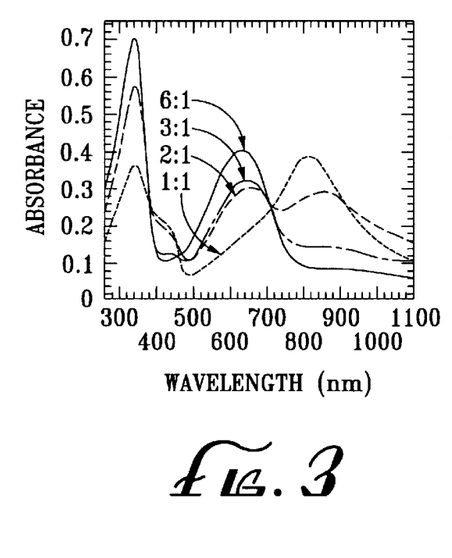
FIG. 3 shows the UV/vis spectra for polyaniline solutions doped with various concentrations of R-camphorsulfonic acid (R-CSA) in n-methyl pyrrolidinone (NMP).
Figure 4:
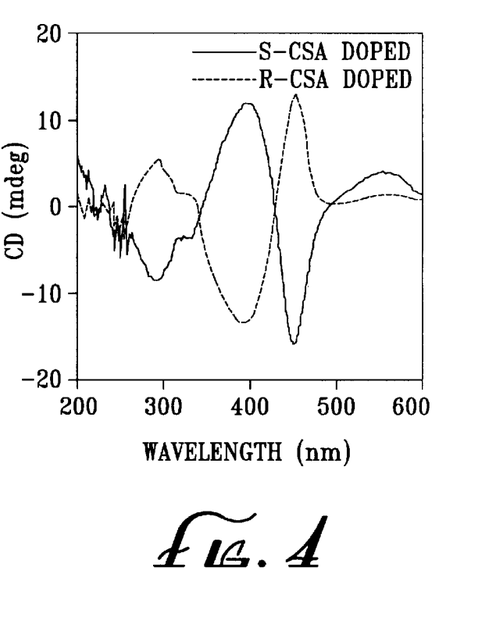
FIG. 4 shows the CD (circular dichromism) spectra for R- and S-doped polyaniline solutions in NMP (polyaniline: CSA=1:1).
Figure 5:
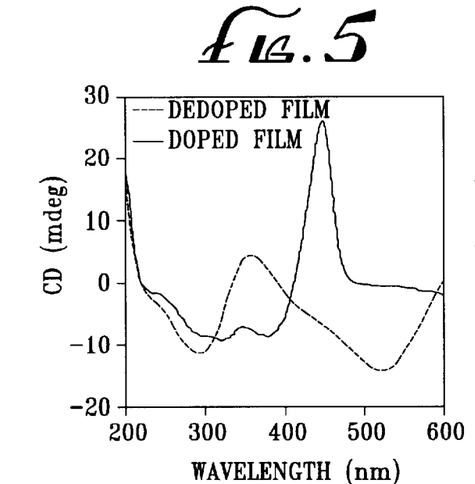
FIG. 5 shows the CD spectra of R-CSA doped and dedoped polyaniline films.

UV/visible spectra were used to follow the doping process of the emeraldine base form of polyaniline with increasing amounts of R-CSA and S-CSA. From FIG. 3 it can be seen that as the concentration of doping acid (in this case R-CSA) increases, the localized exciton peak at 650 nm associated with the electron transition from quinoid rings of the insulating emeraldine base form of polyaniline decreases gradually, and is eventually eliminated. In its place, two optical absorption peaks at 440 nm and 820 nm appear, which are interpreted as excitations of valence electrons to the polaron band formed as emeraldine base is doped to the conducting emeraldine salt form. This is consistent with the two-step transition theory proposed by Stafström et al. where protonation leads to phase segregation of unprotonated and fully protonated domains, followed by a transition from isolated, doubly charged, spinless bipolarons to a polaronic metal. In principle, a 2:1 mixture of polyaniline with CSA should lead to fully doped polyaniline, however, the spectra in FIG. 3 indicate that a 1:1 molar ratio is needed to fully dope polyaniline with CSA in NMP solutions. Molar ratios of 1:2 or more yield spectra comparable to the fully doped 1:1 curve. The circular dichroism (CD) spectra for R-CSA and S-CSA doped polyaniline in NMP solutions are shown in FIG. 4. The R-CSA and the S-CSA spectra are essentially mirror images of each other indicating that these two chiral forms of polyaniline possess opposite handedness. The CD absorbances at 390 and 450 nm are related to the polyaniline chain, while the CD band at 285 nm is caused by free R-CSA and S-CSA in the NMP solutions. The source of the optical activity has been attributed to the conformational properties of the chain backbone in which a helix of opposite rotation is formed. Optically active thin films of R-CSA or S-CSA doped polyaniline can be readily grown on glass plates from the optically active polyaniline/NMP solutions. A representative spectrum of a thin film (1 $\mu$m thick) of polyaniline doped with R-CSA is shown in FIG. 5. A spectrum of this thin film R-CSA doped polyaniline is comparable to the solution spectrum shown in FIG. 4. Dedoping the R-CSA polyaniline film with ammonium hydroxide creates a new chiral form of polyaniline as shown in FIG. 5. The dedoped polyaniline film is stable in air, water and in organic solvents such as isopropanol and acetonitrile. The dedoped polyaniline is also thermally stable as shown by TGA analysis which indicates stability (<5% weight loss) to 350° C. before it decomposes. The chirality is stable to at least 80° C.

Figure 6:
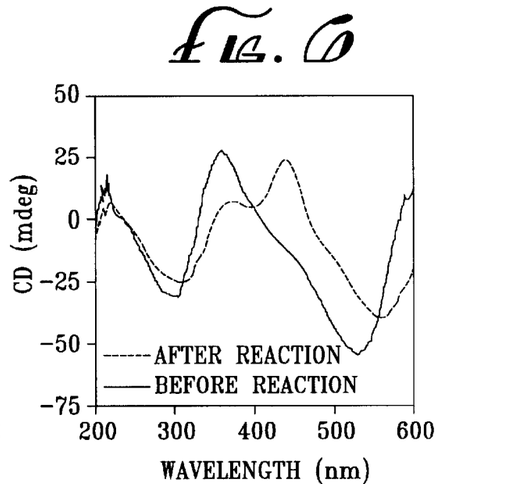
FIG. 6 shows the CD spectra of a dedoped R-CSA polyaniline film before and after treatment with L-phenylalanine.
Figures 7, 8:
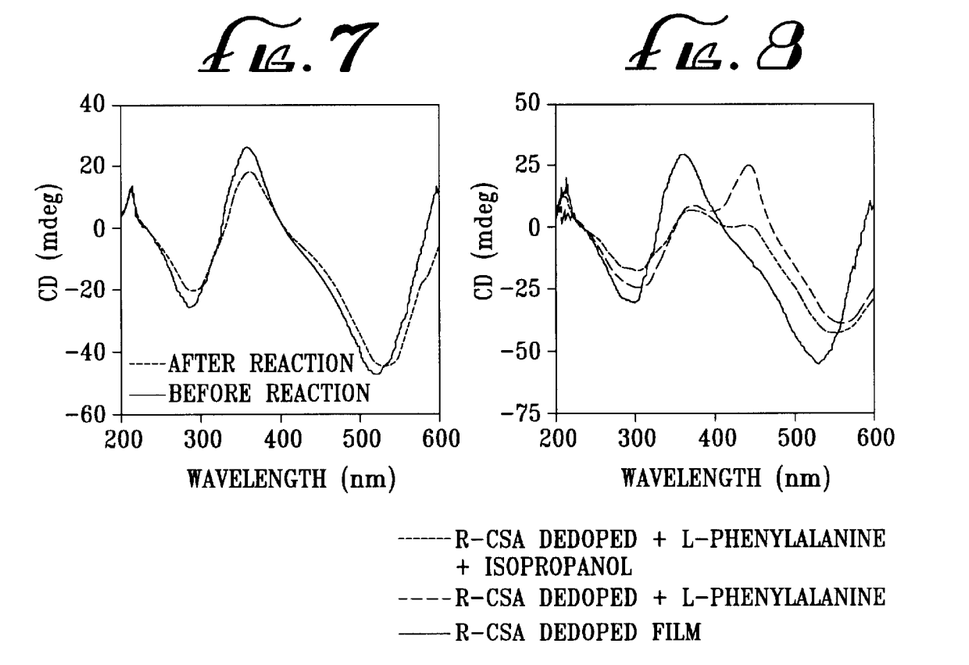
FIG. 7 shows the CD spectra of a dedoped R-CSA polyaniline film before and after treatment with D-phenylalanine.
FIG. 8 shows CD spectra of FIG. 6 and further showing the effect of washing with isopropanol to remove the L-phenylalanine.
Figure 9:
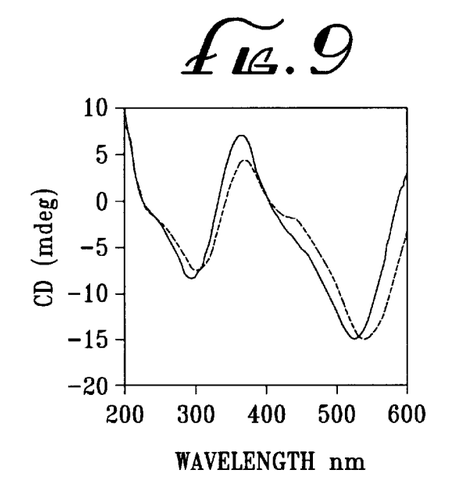
FIG. 9 shows the CD spectrum of a R-CSA polyaniline film before and after treatment with a racemic mixture of DL-o-tyrosine.
Figure 10:
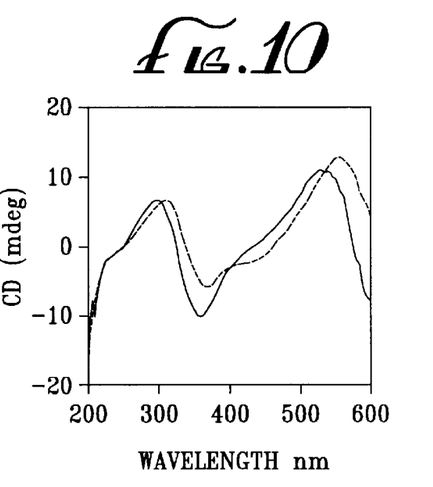
FIG. 10 shows the CD spectrum of a S-CSA polyaniline film before and after treatment with a racemic mixture of DL-o-tyrosine.

The chiral forms of polyaniline generated by doping with R-CSA or S-CSA and then dedoping with base selectively bind one enantiomeric form of an amino acid from its aqueous racemic solution. This can be seen in FIG. 6 where the chiral form (from R-CSA doping/dedoping) selectively binds L-phenylalanine from its aqueous solution. The enhanced CD absorbance at 450 nm indicates a "doping" type interaction. This same chiral form of polyaniline does not complex with D-phenylalanine since no peak enhancement is found at 450 nm as can be seen in FIG. 7. On the other hand, the chiral form of dedoped polyaniline generated by S-CSA has the opposite response and preferentially binds D-phenylalanine as found by an enhanced CD absorbance band around 450 nm (not shown). This S-CSA doped/dedoped form of chiral polyaniline does not interact with L-phenylalanine. When a racemic mixture of DL-phenylalanine is exposed to either R-CSA doped/dedoped polyaniline or S-CSA doped/dedoped polyaniline, an enhanced absorption at 450 nm is observed. Table 1 summarizes the results of the interactions of the R-CSA and S-CSA doped/dedoped forms of chiral polyaniline films with phenylalanine.

TABLE 1

The Interactions of R-CSA and S-CSA Polyaniline Films with Phenylalanine

| Amino Acids/Derivatives | R-CSA Doped/dedoped Polyaniline Film | S-CSA, Doped/dedoped Polyaniline Film |
| --- | --- | --- |
| D-phenylalanine | no | strong |
| L-phenylalanine | strong | no |
| DL-phenylalanine | medium | medium |

The chiral recognition ability is likely due to a helical polyaniline structure created by the chiral dopants. Because of intramolecular hydrogen bonding, the optically active polyaniline films maintain their chiral structure even after the chiral dopants are removed with base. The three-dimensional cavities created in these new chiral forms of polyaniline can selectively recognize and bind one specific enantiomer of an amino acid from its racemic mixture, leaving the other enantiomer in solution. Using an organic solvent, such as isopropanol, the enantiomer bound by the chiral form of polyaniline can be released, as is demonstrated in FIG. 8. The CD spectrum of the chiral dedoped R-CSA polyaniline is shown along with the spectrum observed after exposure to L-phenylalanine and then to isopropanol. The peak that appears at 450 nm on exposing the dedoped polyaniline to L-phenylalanine diminishes considerably after washing with isopropanol. Therefore, this dedoped form of polyaniline possesses a chiral recognition ability which can be used for the separation of enantiomeric amino acids.

In order to study the chiral recognition mechanism in more detail, DL-phenylglycine, DL-proline, DL-histidine and the phenylalanine derivatives, phenylalaninol and phenylalaninamide were investigated. DL-phenylglycine, which has one —$CH_2$— unit less than DL-phenylalanine, has a weaker interaction (i.e., less intensity in the enhanced CD absorbance at 450 nm) with R-CSA and S-CSA doped/dedoped polyaniline compared to DL-phenylalanine. This likely indicates that the chiral recognition ability of dedoped polyaniline is size dependent. To test this assumption, proline and histidine, which have smaller side groups, were used to probe this interaction. Neither proline nor histidine showed any enhanced CD absorbance at 450 nm. Therefore, it appears that chiral dedoped polyaniline has three-dimensional cavities in which only chiral molecules with the right size and chirality can interact with the polymer backbone. Additionally, L-phenylalaninol and L-phenylalaninamide showed significantly less enhanced CD absorbance, indicating that the primary amine and carboxylate groups are necessary for the best chiral recognition.

Figure 11:
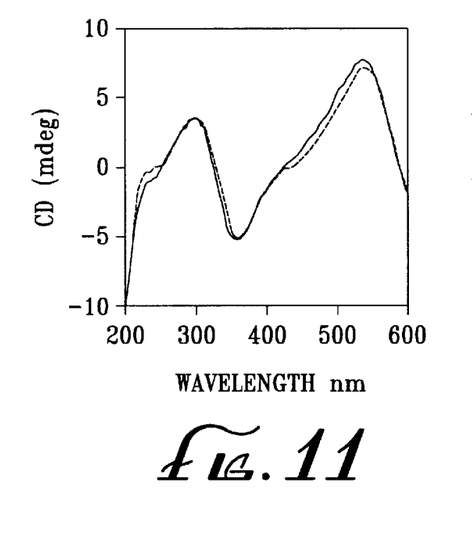
FIG. 11 shows the CD spectrum of a S-CSA polyaniline film before and after treatment with L-tryptophan.
Figure 12:
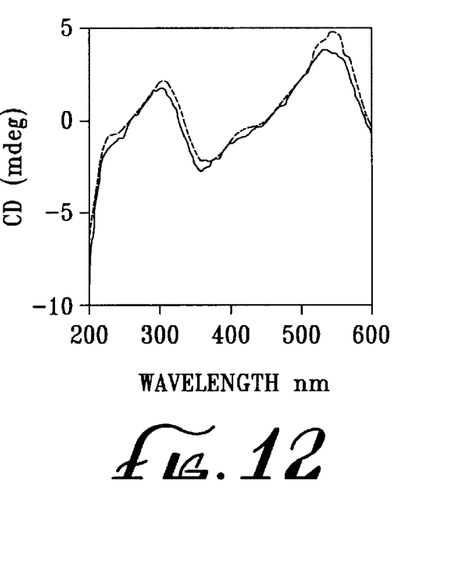
FIG. 12 shows the CD spectrum of a S-CSA polyaniline film before and after treatment with D-tryptophan.
Figure 13:
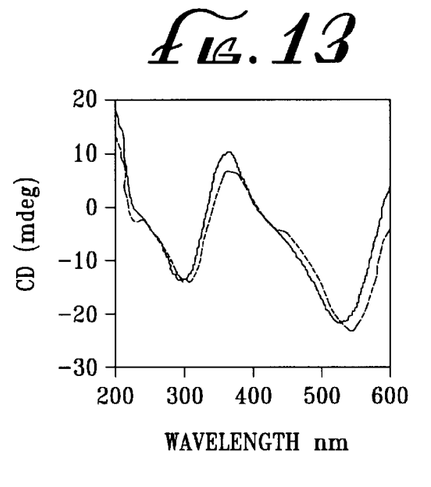
FIG. 13 shows the CD spectrum of a R-CSA polyaniline film before and after treatment with a racemic mixture of DL-tryptophan.
Figure 14:
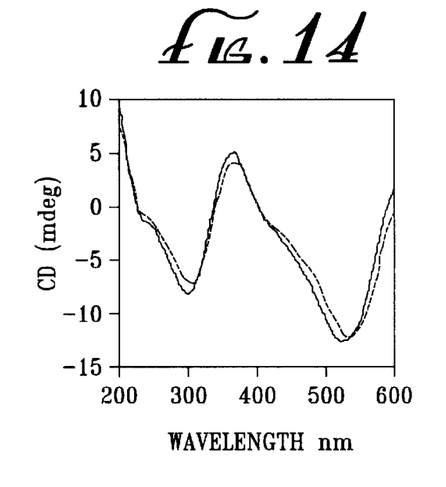
FIG. 14 shows the CD spectrum of a R-CSA polyaniline film before and after treatment with a racemic mixture of DL-leucine.
Figure 15:
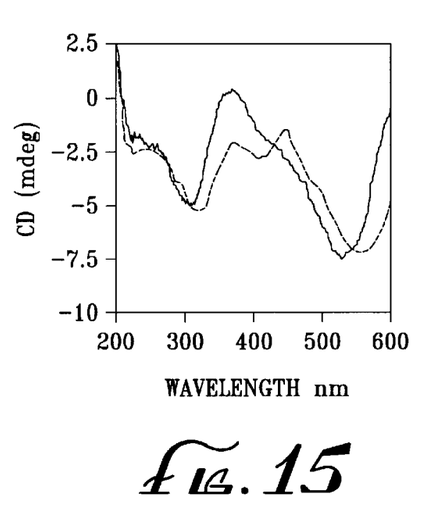
FIG. 15 shows the CD spectrum of a R-CSA polyaniline film before and after treatment with D-tyrosine.
Figure 16:
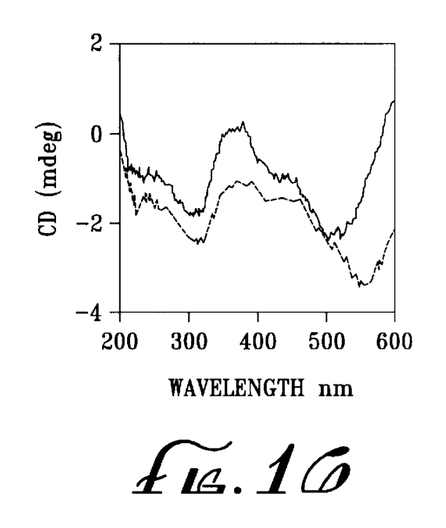
FIG. 16 shows the CD spectrum of a R-CSA polyaniline film before and after treatment with L-tyrosine.

FIGS. 9 through 16 show the use of dedoped polyaniline films on various different amino acids. In particular, since the after-reaction curves (circular dichromism) in FIGS. 9 and 10, which show use of dedoped films formed from complementary chiral forms of the dopant, are different, the D,L mixture of o-tyrosine can be separated as described above. FIGS. 11, 12 and 13 show the different curves for the L- and D-chiral forms of tryptophan on the dedoped S-CSA form of the polyaniline film and the racemic tryptophan mixture on the dedoped R-CSA form of the film. Of significance for separation purposes is the difference between the two curves at a wavelength of 450 nm. For comparison purposes with FIG. 13, FIG. 14 shows the same film with D,L-leucine. FIGS. 15 and 16 show that D-tyrosine can be separated with the dedoped R-camphorsulfonic acid polyaniline film (R-CSA Pani) while the levo-form of tyrosine does not bind to the R-CSA dedoped film. While not shown, the L-tyrosine does bind to the S-CSA dedoped polyaniline film and produces a curve which is the mirror image of that shown in FIG. 16.

Doping polyaniline with either R-CSA or S-CSA creates chiral forms of polyaniline. The chirality is clearly due to the polyaniline backbone since the polymer remains chiral when the dopants are removed. Polyaniline doped with R-CSA and then dedoped interacts preferentially with L-phenylalanine as indicated by a "doping" type absorption band at ~450 nm by CD spectroscopy. No absorption is found when R-CSA doped/dedoped polyaniline interacts with D-phenylalanine. Conversely, polyaniline doped with S-CSA and then dedoped interacts preferentially with D-phenylalanine and has no interaction with L-phenylalanine. Therefore, either type of dedoped polyaniline can be used to separate a racemic mixture of DL-phenylalanine. Since the retained enantiomer of phenylalanine can be released using isoproanol, enantioseparations of amino acids are possible.

Because bacterial racemates and epimerases are capable of catalyzing the conversion of almost all physiological L-amino acids into their D-enantiomers, the fermented foods and beverages produced with the aid of bacterial starters cultures contain D-amino acids, in very high amounts in some cases. The occurrence of D-amino acids is also of interest with respect to their flavor. The D-enantiomers of many amino acids have a sweet taste in contrast to their L-enantiomers, which are frequently bitter. The ratio of the enantiomer of amino acid can, therefore, contribute to the final flavor of fermented foodstuffs. Until recently, no practical methods have been available to detect the D-amino acids in fermented foods. A chiral sensor as described herein can detect qualitatively and quantitatively the contents of D-amino acids in fermented foods, which is of major interest from analytical, biochemical, food biotechnological, and nutritional points of view.

Because a chiral form of polyaniline can selectively bind one enantiomer from a racemic solution of an amino acid, it can be used as a sensor for the detection of existence and amount of D-amino acids in fermented foods. Such a chiral sensor complements the established analytical methods used for food quality and food authentication control and can serve to test the maturation of certain foods and drinks. Further, because humans constantly consume D-amino acids in fermented foods and drinks, there are low but significant amounts of certain D-amino acids detectable in our blood. This chiral sensor has applications in clinical monitoring of D-analytes and in other specific medical measurements (e.g., binding constants of D-amino acids, etc.).

The stereoselectively and stereospecific binding of D-amino acids by a chiral polyaniline thin film coated on an electrode will result in a change of the membrane potential upon complexation. As a result, measurements of the membrane potential change will make it possible to qualitatively and quantitatively detect the D-amino acids.

It is also possible to detect D-amino acids by other direct electrochemical methods. An electrode with a chiral polymer coating that can selectively bind the D-amino acids can be used to measure the electrical potential or amperometrical change, thus making it is possible to detect D-amino acids qualitatively and quantitatively.

The invention is not limited to the separation of chiral mixtures of amino acids. Chiral polyaniline polymers, in film or powder form, can be used to separate a broad range of chiral mixtures.

Figure 17:
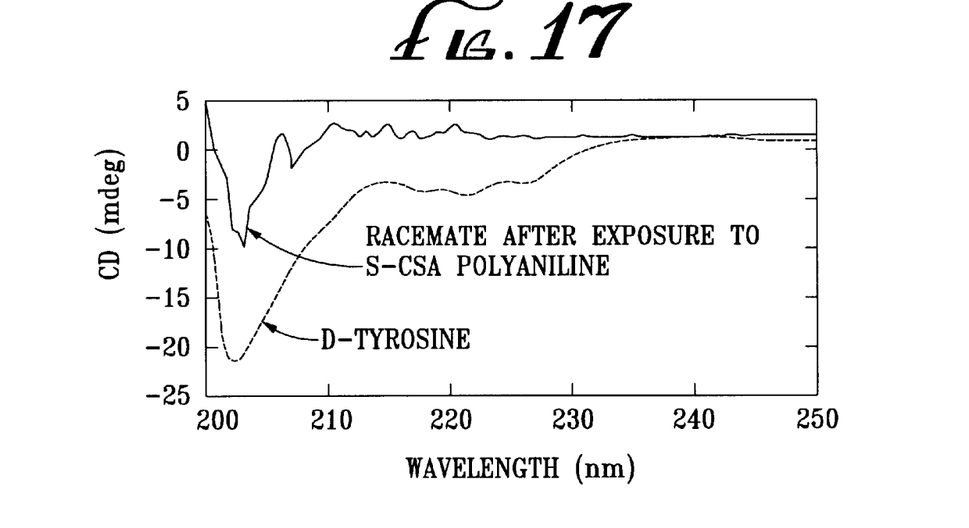
FIG. 17 is a CD spectrum of an extracted DL-o-tyrosine solution after treatment with an S-CSA dedoped polyaniline powder compared to a D-tyrosine standard.

FIG. 17 shows that an enantiomer of tyrosine can be separated from its racemic mixture. A free-standing film (~50 um thick) was formed from polyaniline doped with S-CSA. The S-CSA doped film was ground to a fine powder, dedoped with base and then added to an aqueous solution of a racemic mixture of DL-o-tyrosine (concentration=2 mg/ml). After 60 minutes, the polyaniline powder was removed. The upper curve in FIG. 17 (solid line) is the CD spectrum taken of the resulting solution. The lower curve in FIG. 17 (dashed line) is a CD spectrum of a D-tyrosine standard. It is evidence from the negative CD absorbance that an excess of D-Tyrosine is left in solution. This indicates that S-CSA doped/dedoped polyaniline complexes preferentially with L-tyrosine.

Figure 18:
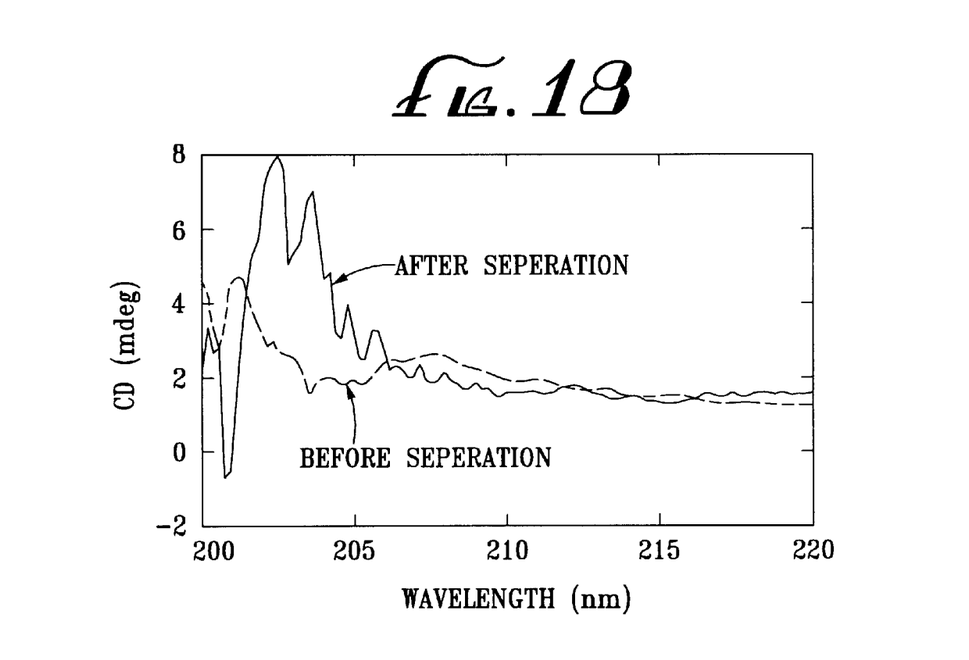
FIG. 18 is a CD spectrum of an extracted DL-dopa solution after treatment with an S-CSA dedoped polyaniline powder compared to the DL-dopa starting mixture.

FIG. 18 demonstrates that chiral polyaniline can be used to separate a racemic mixture of DL-dopa. L-dopa is used to treat the symptoms of Parkinson's disease. A fine powder of S-CSA doped/dedoped ground polyaniline film was put into an aqueous solution of a racemic mixture of DL-dopa (concentration=1 mg/ml). After 60 minutes the polyaniline powder was removed. A CD spectrum of the resulting solution is shown in the upper curve (solid line) in FIG. 18. The CD spectrum of an aqueous solution of DL-dopa racemic mixture is shown as the dashed line in FIG. 18. The markedly enhanced chirality found for the solution is indicative of excess L-dopa and is clearly due to the removal of the other enantiomer (D-dopa) by the S-CSA doped/dedoped polyaniline.

Figure 19:
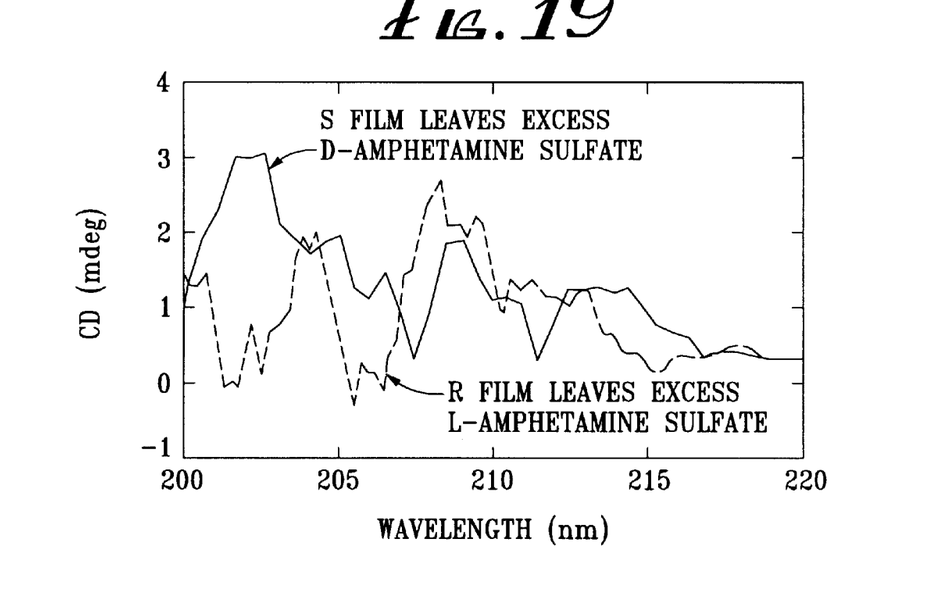
FIG. 19 is a CD spectrum of DL-amphetamine sulfate solution after treatment with either an S-CSA or a R-CSA polyaniline powder.

FIG. 19 demonstrates that chiral polyaniline can be used to separate a racemic mixture of DL-amphetamine sulfate. Amphetamines are central nervous system stimulants. A fine powder of S-CSA doped/dedoped polyaniline ground film was placed in a racemic mixture of DL-amphetamine sulfate aqueous solution. The polyaniline powder was removed after 60 minutes. A CD spectrum of the resulting solution is shown as the solid line in FIG. 19. The chirality created in the solution is due to an excess of D-amphetamine sulfate, as found by comparing the spectrum with that of a standard. This indicates that the S-CSA doped/dedoped polyaniline complexes preferentially with L-amphetamine sulfate. Conversely, R-CSA doped/dedoped polyaniline complexes preferentially with D-amphetamine sulfate. A R-CSA doped/dedoped polyaniline film ground to fine powder was placed in a racemic mixture of DL-amphetamine sulfate for 60 minutes. A CD spectrum taken from the solution after removal of the polyaniline powder is shown as the dashed line in FIG. 19. The chirality created in the solution is due to an excess of L-amphetamine sulfate, as found by comparing the solution spectrum to an L-amphetamine sulfate standard. This indicates that the R-CSA doped/dedoped polyaniline complexes preferentially with D-amphetamine sulfate. Note that the resultant solutions from exposing a racemic mixture of DL-amphetamine sulfate to either R-CSA or S-CSA doped/dedoped polyaniline are both chiral with opposite handedness as can be seen in FIG. 19.

Figure 20:
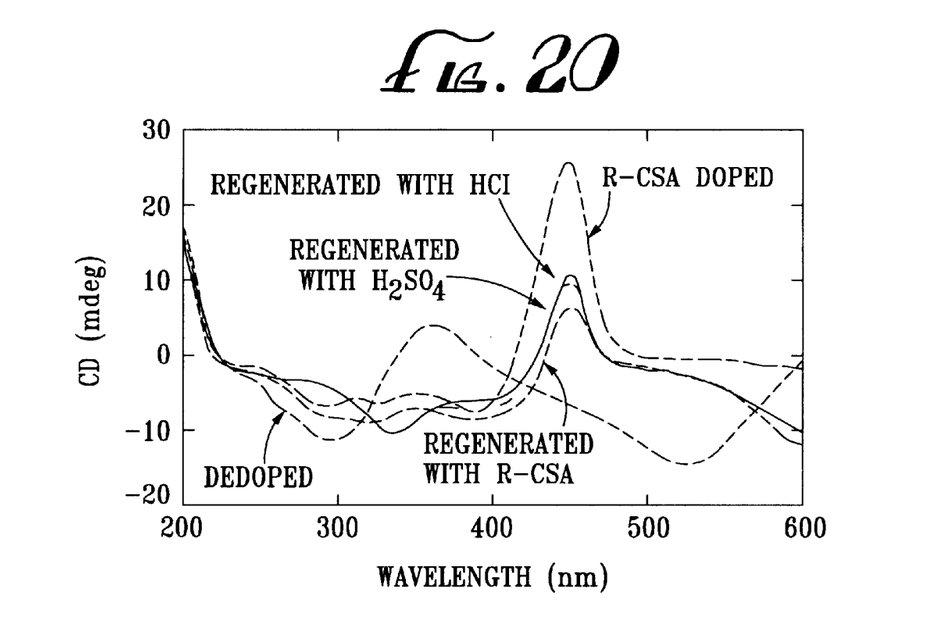
FIG. 20 shows the CD spectrum of a R-CSA doped polyaniline film, that film dedoped using ammonium hydroxide, and that film restored to its doped configuration with R-CSA, $H_2SO_4$ or HCl.

The restoration of chirality is important because it enables batch processing of chiral separations using column chromatography or regeneration of bulk powdered chiral polymer. If, during an operation using the chiral polymer, the chirality of the dedoped polyaniline decreases, the chirality can be restored using any strong acid as is demonstrated in FIGS. 20, 21, 22 and 23. In FIG. 20 the CD spectrum of a R-CSA doped polyaniline polymer is shown along with the CD spectrum of the polyaniline dedoped using 0.1 M ammonium hydroxide. The dopant-induced peak at ~450 nm can be restored by redoping the polyaniline film using R-CSA, $H_2SO_4$ or HCl or other strong acids. The curves in FIG. 20 are obtained on chiral polyaniline restored using 0.1M concentrations of each of the acids. 0.1 M acids do not induce complete redoping. However, the complete intensity of the R-CSA dopant induced peak can be restored by using 1.0 M R-CSA, $H_2SO_4$ or HCl. FIG. 20 clearly demonstrates that any strong acid can be used to restore chirality to R-CSA doped/dedoped polyaniline.

Figure 21:
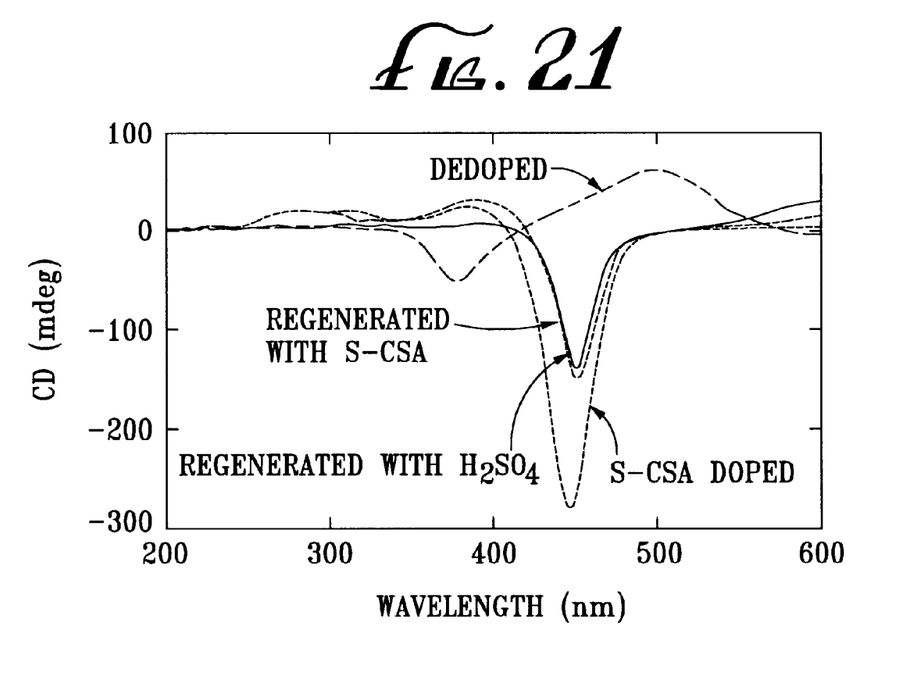
FIG. 21 shows the CD spectrum of a polyaniline film doped with S-CSA, dedoped with $NH_4OH$ and restored using S-CSA or $H_2SO_4$.

Similarly, FIG. 21 demonstrates the restoration of chirality for polyaniline doped with S-CSA. In FIG. 21 the CD spectrum of an S-CSA doped film is shown along with the CD spectrum for polyaniline dedoped using 0.1 M $NH_4OH$. The dopant-induced peak at 450 nm is shown restored by redoping the polyaniline film in either 0.1 M S-CSA or 0.1 M $H_2SO_4$. While low concentration acids were used in the experiments shown in FIG. 21, the complete intensity of the S-CSA dopant induced peak can be restored by using 1.0 M acid. FIG. 21 demonstrates that any strong acid can be used to restore chirality to S-CSA doped/dedoped polyaniline. Note that FIGS. 20 and 21 are essentially mirror images of each other.

Figure 22A:
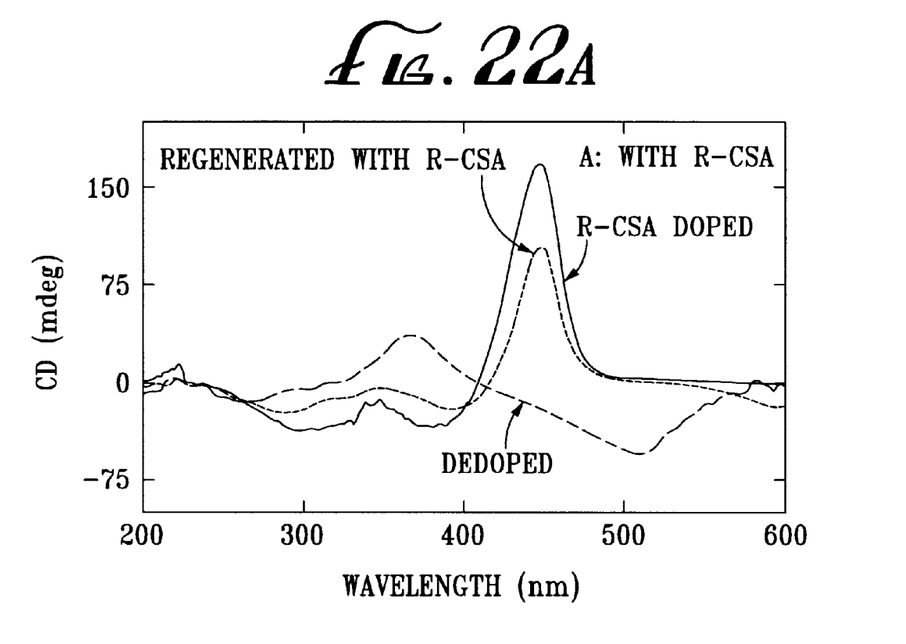
FIG. 22a shows the CD spectrum of a polyaniline film doped with R-CSA and redoped with R-CSA following dedoping.
Figure 22B:
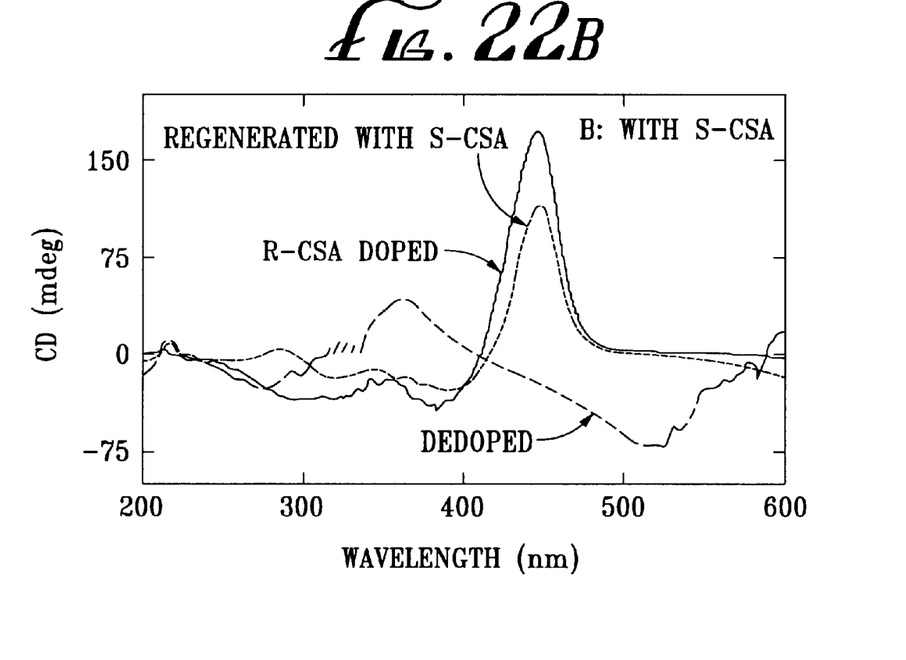
FIG. 22b shows the CD-spectrum of a polyaniline film doped with R-CSA and re-doped with S-CSA following dedoping.

FIGS. 22 and 23 demonstrate that dedoped polyaniline has a unique structure as a result of its method of initial formation. In particular the dedoped polymer has a remarkable memory for the helical sense induced by doping with a chiral acid. In FIG. 22 the peak at 450 nm produced by doping polyaniline with R-CSA is compared to the peak produced by redoping (after dedoping) of the same film with 0.1 M R-CSA. FIG. 22b compares the peak at 450 nm produced by doping polyaniline with R-CSA to the peak produced by redoping the same film with 0.1 M S-CSA. The same helical sense of the polyaniline is restored even when redoping is conducted using the "wrong" acid (i.e., the enantiomer of the original acid used to form the doped film.) This indicates that once the helical sense (chiral form) in polyaniline film is set by curing and cross-linking of the polymer it cannot be changed; the original chirality can simply be restored by any strong acid.

Figure 23A:
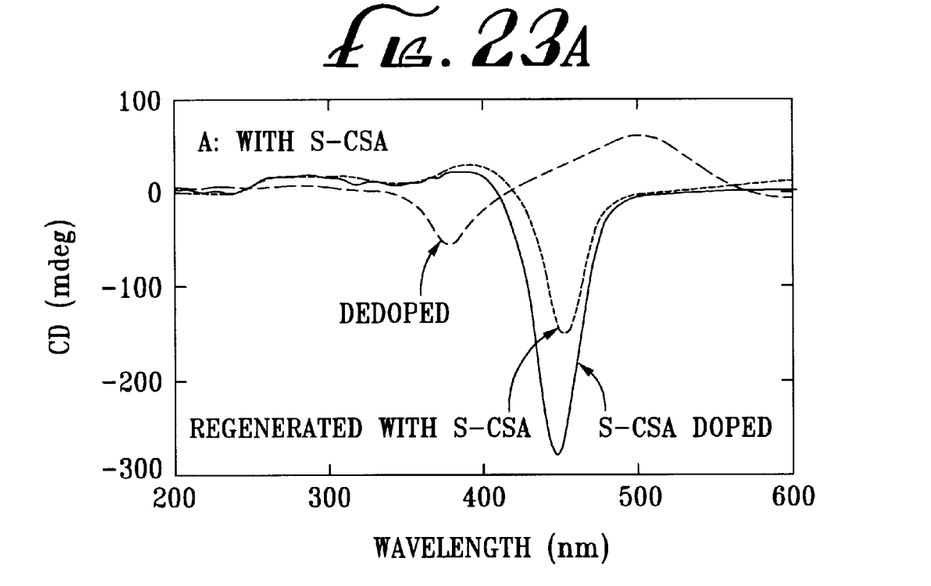
FIG. 23a shows the CD spectrum of a polyaniline film doped with S-CSA and re-doped with S-CSA following dedoping.
Figure 23B:
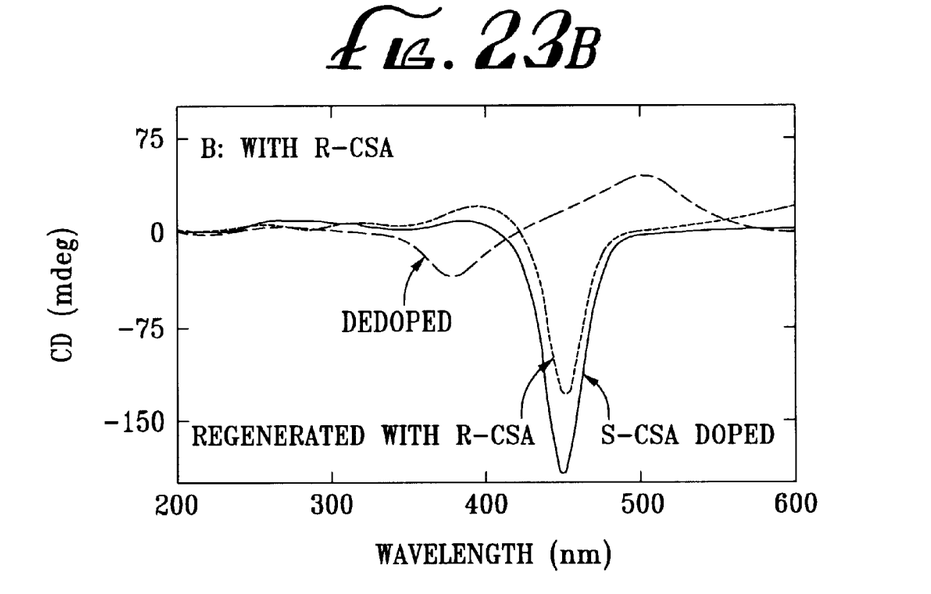
FIG. 23b shows the CD spectrum of a polyaniline film doped with S-CSA and re-doped with R-CSA following redoping.

The same memory effect for polyaniline doped with S-CSA is shown in FIG. 23. In FIG. 23a the peak at 450 nm produced by doping polyaniline with S-CSA is compared to the peak produced by redoping (after dedoping) of the same film with 0.1 M S-CSA. FIG. 23b compares the same peak at 450 nm produced by doping polyaniline with S-CSA to the peak produced by redoping these same film with 0.1 M R-CSA. Again the same helical sense of polyaniline is restored even when redoping with the "wrong" acid.

Further, it has been shown that the chiral separation properties of the dedoped polyaniline are not necessarily the result of the formation of a membrane or film with a pore structure which will allow passage of one enantiomeric form. The exact nature of the attachment of the extracted enantiomer form is not known. However, as demonstrated by FIGS. 17–19, powdered, dedoped polyaniline added to solutions of a chiral mixture preferentially adsorbs or otherwise reversibly binds to particle surfaces of one of the enantiomeric forms and, as shown in FIGS. 20–23, the bound form depends only on the chiral acid used to initially convert achiral polyaniline to doped polyaniline.

Although the present invention has been described in considerable detail with reference to certain preferred versions and uses thereof, other versions and uses are possible. For example, while R- and S-camphorsulfonic acid have been used in the above examples, one skilled in the art will recognize, based on the teachings hereinabove, that other chiral dopants can be used to produce doped polyaniline materials with different surface properties. Once dedoped, these materials can be used to separate different enantiomers of amino acids or other chiral mixtures. Other suitable chiral acids for doping polyaniline are D- or L-tartaric acid, D- or L-dibenzoyltartaric acid, (15)-(+)-3bromocamphor-10-sulfonic acid, 2-amino-7,7-dimethylbicyclop[2,2,1]heptan-1-methylene sulfonic acid and 2-acrylamide-7,7-dimethylbicyclo[2,2,1] heptan-1-methylene sulfonic acid. Generally speaking, if a chiral organic acid is a strong acid ($pK_a$<3) and soluble in NMP, DMSO or DMF, it can be used to generate chiral polyaniline. Therefore, other hydroxy and sulfonic acids should be suitable dopants. As demonstrated above the same technique and procedure can be used to separate other chiral compounds, including many pharmaceuticals. The range of chiral mixtures which can be separated using dedoped polyaniline materials is broad and those skilled in the art can readily identify enantiomers separable using the teachings herein. This invention is not limited to the separation of amino acids or the pharmaceutical products specifically disclosed. Therefore, the spirit and scope of the appended claims should not be limited to the description of the preferred versions contained herein.

What is claimed is:

1. A polymeric material capable of selectively and reversibly retaining one enantiomeric form of a compound contained in a racemic mixture of that compound wherein said polymeric material is formed by a) dissolving a polymer in an organic solvent along with a chiral dopant to form a chiral doped polymer solution, b) removing the solvent to form a doped polymeric material and c) removing the chiral dopant from the doped polymeric material to form a dedoped polymeric material with selective chiral attachment properties.

2. The polymeric material of claim 1 wherein the method of formation includes coating a substrate with the chiral doped polymer solution prior to removal of the solvent.

3. The polymeric material of claim 1 wherein the method of formation includes the further step of converting the doped polymeric material or the dedoped polymeric material to a powdered form.

4. The polymeric material of claim 1 wherein the polymer is polyaniline.

5. The polymeric material of claim 1 wherein the chiral dopant is the R-or S-form of camphorsulfonic acid.

6. The polymeric material of claim 1 wherein the chiral dopant is the D- or L-form of a hydroxy acid.

7. The polymeric material of claim 6 wherein the hydroxy acid is tartaric acid or dibenzoyl tartaric acid.

8. The polymeric material of claim 1 wherein the chiral dopant is removed by exposing the doped film to a basic solution.

9. The polymeric material of claim 8 wherein the basic solution is a 0.1 Molar Ammonium hydroxide solution.

10. A chiral selective material comprising a dedoped polyaniline, formed by depositing a film on a substrate from a solution containing polyaniline and a chiral organic acid, the dedoped polyaniline being created by extracting the chiral organic acid out of the film with a base after the film is deposited, said dedoped polyaniline film being dried onto the substrate's surface.

11. A chiral selective material comprising a powdered dedoped polyaniline polymer, said material formed by mixing a chiral organic acid with polyaniline in a solvent, evaporating the solvent to solidify a doped polyaniline film, extracting the organic acid to form a dedoped material, and converting the dedoped material to a powder form.

12. The chiral selective material of claim 10 wherein the chiral organic acid is selected from the group consisting of R- or S-sulfonic acid and D- or L-hydroxy acid.

13. The chiral selective film of claim 12 wherein the hydroxy acid is D- or L-tartaric acid or D- or L-dibenzoyl tartaric acid and the R- or S-sulfonic acid is R- or S-camphorsulfonic acid.

14. A chiral selective polyaniline polymer.

15. A chiral selective material comprising a powdered dedoped polyaniline polymer, said material formed by mixing a chiral organic acid with polyaniline in a solvent, evaporating the solvent to form a powdered doped polyaniline film and extracting the organic acid to form a dedoped, powdered polymeric material.

16. The chiral selective material of claim 11 wherein the chiral organic acid is selected from the group consisting of R- or S-sulfonic acid and D- or L-hydroxy acid.

17. The chiral selective material of claim 16 herein the chiral organic acid is selected from the group consisting of R- or S-sulfonic acid and D- or L-hydroxy acid.

* * * * *